(12) United States Patent
Ma et al.

(10) Patent No.: US 11,666,735 B2
(45) Date of Patent: *Jun. 6, 2023

(54) INTRODUCER NEEDLE WITH NOTCHES FOR IMPROVED FLASHBACK

(71) Applicant: Becton, Dickinson and Company, Franklin Lakes, NJ (US)

(72) Inventors: Yiping Ma, Layton, UT (US); Bryan G. Davis, Sandy, UT (US); Weston F. Harding, Lehi, UT (US); Jonathan Karl Burkholz, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 7 days.

This patent is subject to a terminal disclaimer.

(21) Appl. No.: 16/951,819

(22) Filed: Nov. 18, 2020

(65) Prior Publication Data

US 2021/0069476 A1    Mar. 11, 2021

Related U.S. Application Data

(62) Division of application No. 15/946,593, filed on Apr. 5, 2018, now Pat. No. 10,869,993.

(51) Int. Cl.
*A61M 25/06*   (2006.01)
*A61M 5/158*   (2006.01)

(52) U.S. Cl.
CPC ............ *A61M 25/06* (2013.01); *A61M 5/158* (2013.01); *A61M 25/065* (2013.01); *A61M 25/0606* (2013.01); *A61M 25/0693* (2013.01)

(58) Field of Classification Search
CPC .............. A61M 25/06; A61M 25/0606; A61M 25/0612; A61M 25/0693; A61M 25/065;
(Continued)

(56) References Cited

U.S. PATENT DOCUMENTS

| 4,046,144 A | * | 9/1977 | McFarlane | ........ | A61M 25/0693 |
|  |  |  |  |  | 604/168.01 |
| 5,810,780 A | * | 9/1998 | Brimhall | ........... | A61M 39/0606 |
|  |  |  |  |  | 604/272 |

(Continued)

FOREIGN PATENT DOCUMENTS

| DE | 69406333 | 2/1998 |
| EP | 0806221 | 11/1997 |

(Continued)

*Primary Examiner* — Rebecca E Eisenberg
*Assistant Examiner* — Antarius S Daniel
(74) *Attorney, Agent, or Firm* — Kirton McConkie; Whitney Blair; Kevin Stinger

(57) ABSTRACT

An introducer needle may include a proximal end, a distal tip, and a needle lumen extending therebetween. The introducer needle may include a wall defining the needle lumen, a first notch formed through the wall, and a second notch formed through the wall. A catheter system may include a catheter adapter, a catheter extending distally from the distal end of the catheter adapter, a flash chamber coupled to the introducer needle, and the introducer needle, which may extend through the catheter. The first and second notches and the flash chamber may facilitate pressure-driven blood flow into the catheter for improved flashback and detection of transfixation when the catheter is primed prior to insertion into vasculature of a patient or otherwise.

20 Claims, 7 Drawing Sheets

(58) Field of Classification Search
CPC .......... A61M 25/0028; A61M 25/0029; A61M
25/003; A61M 25/0032; A61M 25/0071;
A61M 25/0074; A61M 2005/3112; A61M
5/158; A61M 2025/0004; A61M
2025/0006; A61M 2025/0018; A61M
2025/0039; A61M 2025/0073; A61M
2025/0037; A61M 2025/0057; A61K 9/00
See application file for complete search history.

(56) References Cited

U.S. PATENT DOCUMENTS

| | | | |
|---|---|---|---|
| 7,670,317 B2 | 3/2010 | Cindrich | |
| 2003/0153874 A1 | 8/2003 | Tai | |
| 2007/0083162 A1* | 4/2007 | O'Reagan | A61M 39/26 604/167.03 |
| 2010/0168675 A1 | 7/2010 | Cindrich et al. | |
| 2011/0313357 A1 | 12/2011 | Skutnik et al. | |
| 2012/0016296 A1 | 1/2012 | Charles | |
| 2013/0261554 A1 | 10/2013 | Baid | |
| 2014/0081210 A1 | 3/2014 | Bierman et al. | |
| 2015/0202422 A1 | 7/2015 | Ma et al. | |
| 2015/0209550 A1* | 7/2015 | Teh | A61M 25/0069 604/523 |
| 2017/0120001 A1 | 5/2017 | Hyer et al. | |
| 2017/0239443 A1 | 8/2017 | Abitabilo et al. | |

FOREIGN PATENT DOCUMENTS

| | | |
|---|---|---|
| EP | 2260897 | 12/2010 |
| JP | H10-033686 | 2/1998 |
| JP | 2012517326 | 8/2012 |
| JP | 2016511083 | 4/2016 |
| WO | 2017074683 | 5/2017 |

* cited by examiner

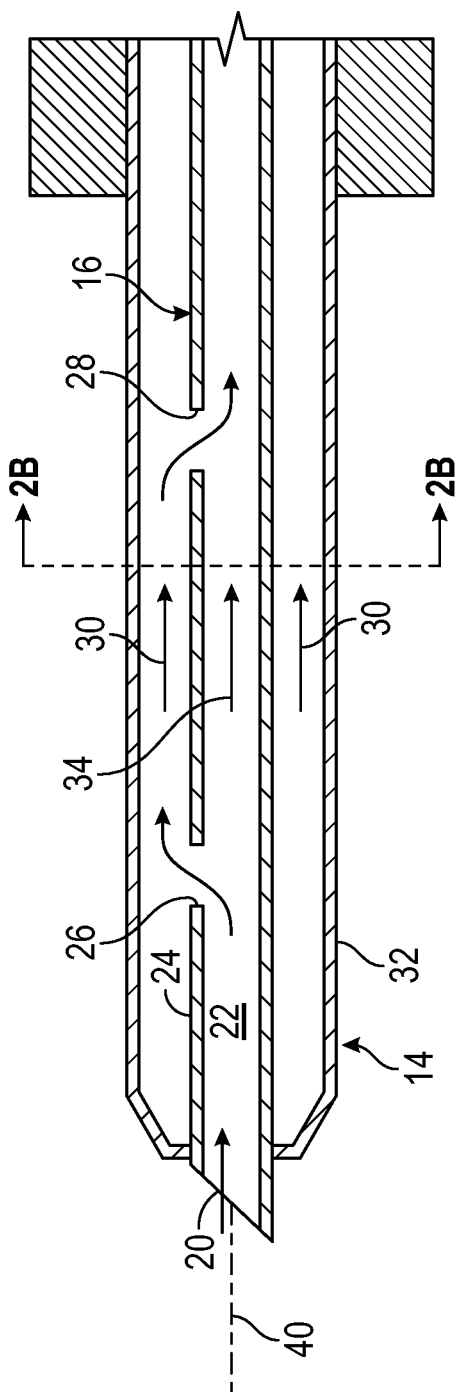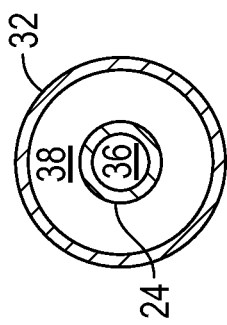
FIG. 2A
FIG. 2B

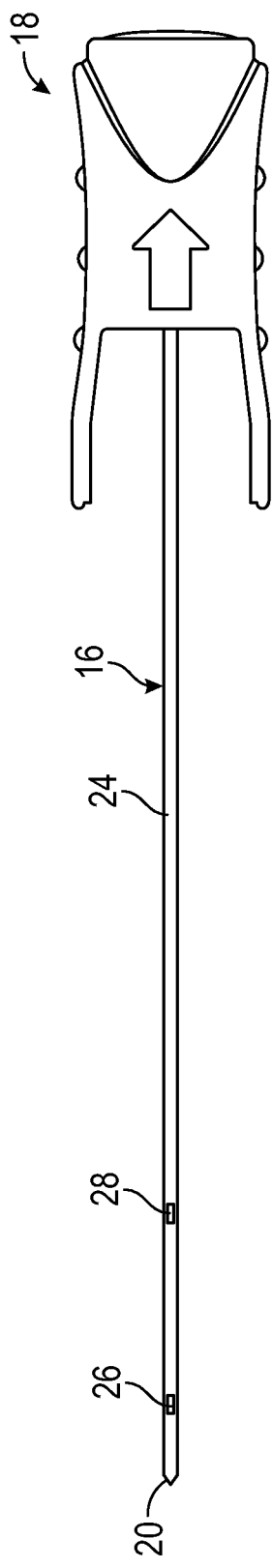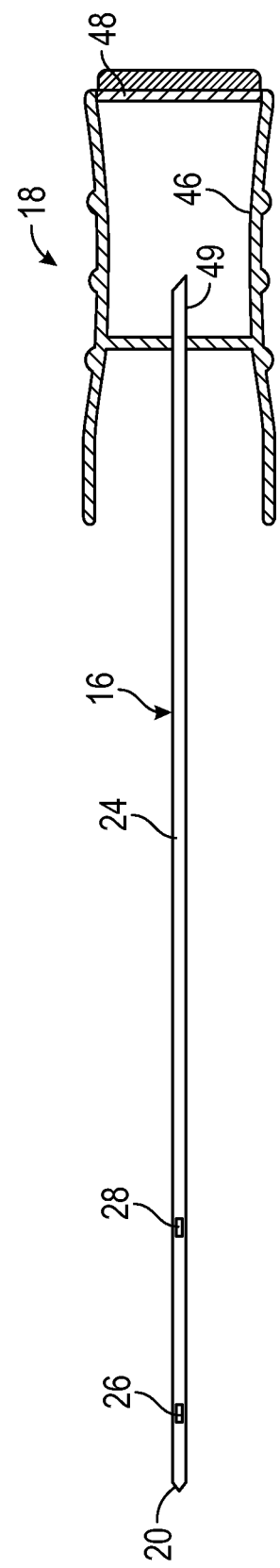
FIG. 3A
FIG. 3B

INTRODUCER NEEDLE WITH NOTCHES FOR IMPROVED FLASHBACK

RELATED APPLICATIONS

This application is a divisional of U.S. patent application Ser. No. 15/946,593, filed Apr. 5, 2018, and titled INTRODUCER NEEDLE WITH NOTCHES FOR IMPROVED FLASHBACK, which is incorporated herein in its entirety.

BACKGROUND OF THE INVENTION

Intravenous (IV) catheters are commonly used for a variety of infusion therapies. For example, IV catheters may be used for infusing normal saline solution, various medicaments, or total parenteral nutrition into a patient. IV catheters may also be used for withdrawing blood from the patient.

A common type of IV catheter is an over-the-needle peripheral IV catheter. As its name implies, the over-the-needle peripheral IV catheter may be mounted over an introducer needle having a sharp distal tip. The sharp distal tip may be used to pierce skin and a vasculature of the patient. Insertion of the IV catheter into the vasculature may follow the piercing of the vasculature by the introducer needle. The introducer needle and the IV catheter are generally inserted at a shallow angle through the skin into the vasculature of the patient with a bevel of the introducer needle facing away from the skin of the patient.

In order to verify proper placement of the introducer needle and/or the IV catheter in the vasculature, a clinician generally confirms that there is flashback of blood, which may be visible to the clinician. In some instances, the introducer needle may include a single notch, and in response to the distal tip of the introducer needle being positioned within the vasculature, blood may flow proximally through a needle lumen, exit the needle lumen through the notch, and then travel proximally between an outer surface of the introducer needle and an inner surface of another device (e.g., the IV catheter). Accordingly, where the other device is at least partially transparent, the clinician may visualize a small amount of blood "flashback" and thereby confirm placement of the catheter within the vasculature. Presence of a vasculature entrance indicator, such as flashback, may facilitate successful placement of IV catheters. Once placement of the introducer needle within the vasculature has been confirmed, the clinician may temporarily occlude flow in the vasculature and withdraw the introducer needle, leaving the catheter in place for future blood withdrawal and/or fluid infusion.

In some markets, priming of the IV catheter is common practice. In order to prime the IV catheter, the clinician may fill the IV catheter with saline or another priming fluid to reduce or eliminate any air pockets disposed within the IV catheter. The saline may also fill a portion of a needle lumen proximate the notch, as well as distal to the notch, all the way to the distal tip of the introducer needle. Thus, when the distal tip of the introducer needle enters the vasculature, flashback may be slowed due to diffusion. Flashback may also be difficult to visualize due to mixing of flashback with the saline.

Furthermore, many integrated IV catheter systems having an integrated extension tube do not include a flash chamber, which may be vented. Examples of integrated IV catheter systems may include, for example, the BD NEXIVA™ Closed IV Catheter System, the BD NEXIVA™ DIFFUSICS™ Closed IV Catheter System, or the Becton Dickinson PEGASUS™ Safety Closed IV Catheter System. Thus, after the priming of the IV catheter, the IV catheter system may no longer be vented, and when the distal tip of the introducer needle enters the vasculature, blood may only slowly diffuse into the introducer needle. Also, transfixation of the vasculature may not be observed since the proximal diffusion of the blood may continue even when the distal tip is no longer properly placed within the vasculature.

It is to be understood that both the foregoing general description and the following detailed description are exemplary and explanatory and are not restrictive of the invention, as claimed.

BRIEF SUMMARY OF THE INVENTION

The present disclosure relates generally to an introducer needle having a first notch and a second notch, and related devices, systems, and methods. In some embodiments, the introducer needle may include a proximal end, a distal tip, and a needle lumen extending between the proximal end and the distal tip. In some embodiments, the introducer needle may include a wall, which may define the needle lumen. In some embodiments, the first notch may be formed through the wall, and the second notch may be formed through the wall. In some embodiments, the second notch may be proximal to the first notch.

In some embodiments, a catheter system may include a catheter adapter, which may include a distal end, a proximal end, and a lumen extending between the distal end and the proximal end. In some embodiments, the catheter system may include a catheter, which may include an IV catheter, such as a peripheral IV catheter, for example. In some embodiments, the catheter may extend distally from the distal end of the catheter adapter. In some embodiments, the catheter system may include the introducer needle, which may extend through the catheter and beyond the distal end of the catheter when the introducer needle is in an insertion position for insertion into vasculature of a patient.

In some embodiments, the first notch of the introducer needle may be disposed within the catheter when the introducer needle is in the insertion position. In some embodiments, at least a portion of the catheter may be transparent. In some embodiments, where the proximal end of the introducer needle is vented such that air and/or fluid may travel proximally through the introducer needle, presence of the first and second notches may facilitate pressure-driven blood flow into the catheter for improved flashback and detection of transfixation. In some embodiments, the first and second notches may improve first needle stick success by improving the quality of flashback.

In further detail, in some embodiments, the catheter system may include a first fluid pathway, which may extend from the first notch to the second notch between an outer surface of the introducer needle and an inner surface of a wall of the catheter, and a second fluid pathway, which may extend from the first notch to the second notch within the needle lumen. During flashback, blood may flow through the first fluid pathway and/or the second fluid pathway. In some embodiments, the first fluid pathway may provide pressure-driven flashback, even after the catheter system is primed. In some embodiments, flashback may be faster through the first fluid pathway than the second fluid pathway. In some embodiments, flashback through the first fluid pathway may be visible due to the transparency of the catheter.

In some embodiments, the first fluid pathway may have a larger volume than the second fluid pathway, which may facilitate faster flashback through the first fluid pathway than the second fluid pathway. In some embodiments, a cross-section taken through the catheter system perpendicular to a central axis of the catheter system and between the first notch and the second notch may include a needle lumen area and another area between the outer surface of the introducer needle and the inner surface of the wall of the catheter. In some embodiments, the other area may be greater than the needle lumen area. In some embodiments, the other area may be greater than the needle lumen area in each cross-section taken through the catheter system perpendicular to the central axis along an entire length between the first notch and the second notch.

In some embodiments, the catheter system may include a flash chamber, which may facilitate flashback. In some embodiments, the flash chamber may be in fluid communication with the needle lumen. In some embodiments, the flash chamber may include a gas permeable vent. In some embodiments, the gas permeable vent of the flash chamber may provide the venting that allows air and/or fluid to travel proximally through the introducer needle. In some embodiments, the flash chamber may be disposed proximal to the proximal end of the introducer needle. In some embodiments, the gas permeable vent may provide at least some resistance to air flow.

In some embodiments, the catheter may be primed prior to insertion of the catheter and introducer needle into the vasculature of the patient. In some embodiments, the catheter may be primed when the introducer needle is in the insertion position. In some embodiments, in order to prime the catheter, the user may fill the catheter with a priming fluid, such as, for example, saline, to reduce or eliminate any air pockets disposed within the catheter. In some embodiments, the priming fluid may be disposed in a first portion of a needle lumen proximate the first notch and including the distal tip of the introducer needle. Additionally, in some embodiments, the priming fluid may be disposed in a second portion of the needle lumen proximate the second notch. In some embodiments, when the gas permeable vent provides the resistance, the priming fluid in the first portion may be separated from the priming fluid in the second portion, and air may be disposed between the first portion and the second portion in the needle lumen.

In some embodiments, in response to the distal tip of the introducer needle entering the vasculature, blood pressure will drive the flashback into the needle. Additionally, in some embodiments, at least some of the flashback may then be driven out of the introducer needle at the first notch and into the catheter. Furthermore, in some embodiments, in response to the distal tip of the introducer needle entering the vasculature, the priming fluid outside the introducer needle and within the catheter tube between the first notch and the second notch may be driven into the introducer needle through the second notch and may eventually reach the flash chamber. In some embodiments, in response to the distal tip of the introducer needle entering the vasculature, blood may flow proximally through the needle as well. In some embodiments, the pressure-driven blood flow through the first fluid pathway, which may initially be filled with the priming fluid, may be faster than diffusion.

In some embodiments, the flash chamber may include a large, non-restrictive volume, which may facilitate the pressure-driven flow of the priming fluid and/or blood towards or into the flash chamber. In some embodiments, a volume of the flash chamber may be large enough to hold the priming fluid disposed outside the introducer needle and within the catheter between the first notch and the second notch and/or the priming fluid that may travel into the flash chamber during priming of the catheter. Additionally, in some embodiments, the volume of the flash chamber may be large enough to hold blood when the distal tip of the introducer needle is disposed within the vasculature.

In some embodiments, a portion of the wall of the introducer needle between the first notch and the second notch may be pinched or crimped such that fluid, such as blood, is prevented from flowing in the needle lumen between the first notch and the second notch. In some embodiments, the crimped portion of the wall may facilitate rapid flashback through the first fluid pathway.

In some embodiments, the second notch may be disposed within the catheter when the needle is in the insertion position. In some embodiments, the second notch may be disposed within the lumen of the catheter adapter when the needle is in the insertion position. In some embodiments, a distance between the first notch and the second notch may be greater than a length of the catheter, which may facilitate visibility of transfixation.

In some embodiments, the catheter system may include a needle hub, which may be coupled to the catheter adapter when the introducer needle is in the insertion position. In some embodiments, a proximal end of the introducer needle may be secured within the needle hub. In some embodiments, the flash chamber may be disposed within the needle hub.

In some embodiments, the catheter system may include a blood control septum, which may be disposed within the lumen of the catheter adapter. In some embodiments, the septum may divide the lumen of the catheter adapter into a proximal chamber and a distal chamber. In some embodiments, the second notch may be disposed distal to the septum when the introducer needle is in the insertion position.

In some embodiments, the catheter adapter may include a gas permeable vent, which may be selectively opened and/or closed. In some embodiments, the gas permeable vent of the catheter adapter may be disposed distal to the septum such that air in the distal chamber may freely flow out of the gas permeable vent when the vent is opened. In some embodiments, the gas permeable vent of the catheter adapter may be opened during priming of the catheter, which may prevent the priming fluid from being disposed in the first portion of the needle proximate the first notch and/or the second portion of the needle proximate the second notch, as the gas permeable vent of the catheter adapter may provide a path of low resistance for the priming fluid.

In some embodiments, the catheter system may include a seal, which may be secured within the lumen of the catheter adapter. In these and other embodiments, the portion of the wall of the introducer needle between the first notch and the second notch may be pinched or crimped such that fluid is prevented from flowing in the needle lumen between the first notch and the second notch. In some embodiments, the introducer needle may be rotatable from a priming position to the insertion position and/or from the insertion position to the priming position. In some embodiments, the introducer needle may be disposed in the priming position during priming of the catheter and may be disposed in the insertion position during insertion into the vasculature.

In some embodiments, when the introducer needle is in the priming position, the seal may cover and seal the second notch, which may prevent fluid from flowing through the second notch. In some embodiments, when the introducer needle is in the insertion position, the seal may not cover or seal the second notch and fluid may flow through the second notch. In some embodiments, in response to the second notch being uncovered or unsealed, rapid flashback may occur with blood flowing into the needle lumen via the second notch. In some embodiments, the seal may include a septum or flapper.

In some embodiments, the introducer needle may be rotatable between the priming position and the insertion position about the central axis of the catheter system, which may extend through the needle lumen. In some embodiments, the introducer needle may be rotated by twisting the needle hub. In some embodiments, the introducer needle may be rotated in a first direction and/or a second direction opposite the first direction. In some embodiments, the second notch may be aligned with the seal when the introducer needle is in the priming position and the insertion position. In these and other embodiments, the introducer needle may extend a same distance from the distal tip of the catheter when the introducer needle is in the priming position as when the introducer needle is in the insertion position.

In some embodiments, the catheter system may include a plug constructed of a dissolvable material. In some embodiments, the plug may be disposed on top of the second notch to seal the second notch during priming of the catheter system.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 2A is a cross-sectional view of an example introducer needle disposed within a an example catheter, illustrating the introducer needle in the insertion position, according to some embodiments;

FIG. 2B is a cross-sectional view along line 2B-2B of FIG. 2A, according to some embodiments;

FIG. 3A is a top view of an example needle assembly, according to some embodiments;

FIG. 3B is a partial cutaway view of the needle assembly of FIG. 3A, according to some embodiments;

DETAILED DESCRIPTION OF THE INVENTION

Figure 1:
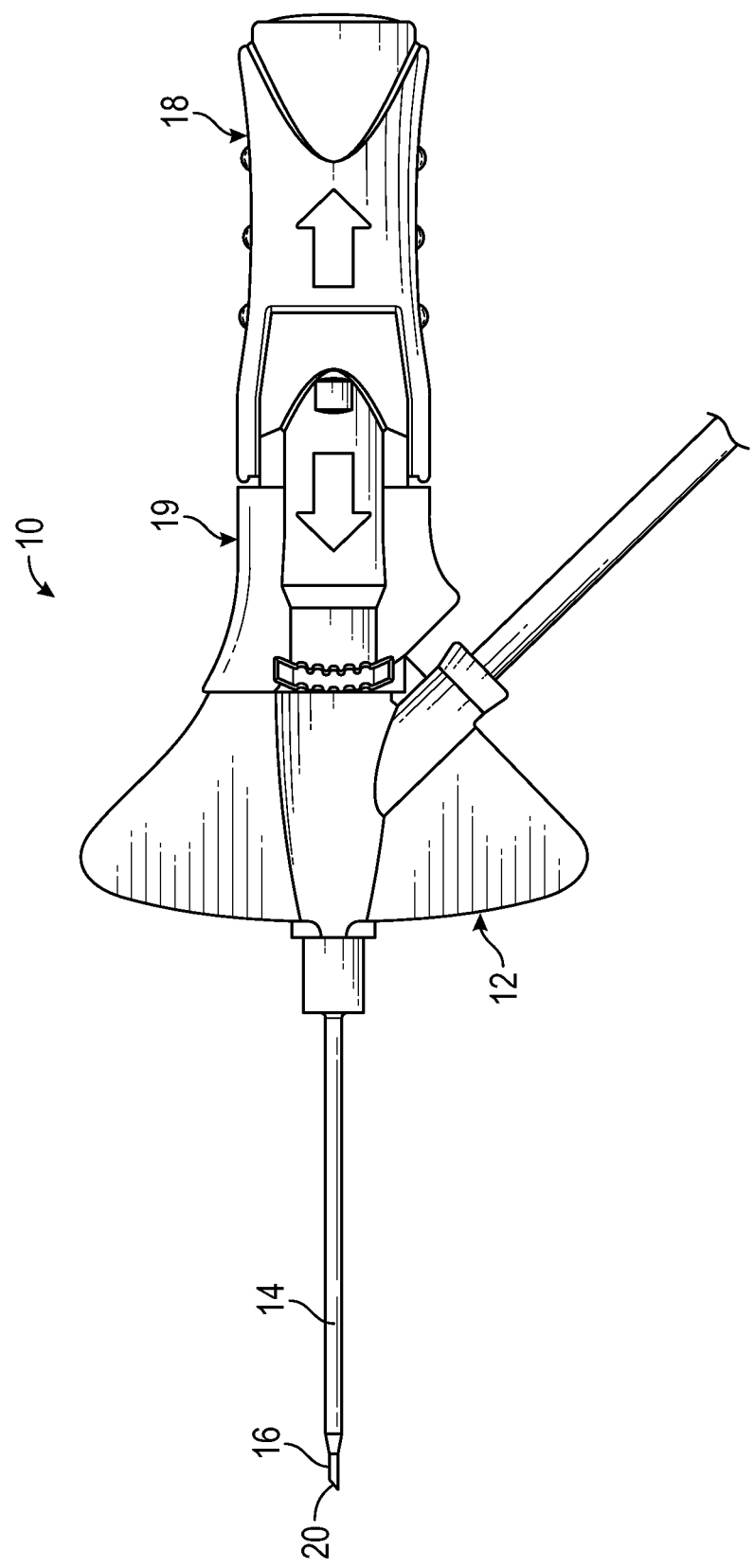
FIG. 1 is a top view of an example catheter system, illustrating the catheter system in an insertion position, according to some embodiments.

The present disclosure relates generally to an introducer needle having a first notch and a second notch, and related devices, systems, and methods. Referring now to FIG. 1, in some embodiments, a catheter system 10 may include a catheter adapter 12, which may include a distal end, a proximal end, and a lumen extending between the distal end and the proximal end. In some embodiments, the catheter system 10 may include a catheter 14, which may include an IV catheter, such as a peripheral IV catheter, for example. In some embodiments, the catheter 14 may extend distally from the distal end of the catheter adapter 12. In some embodiments, the catheter system 10 may include the introducer needle 16, which may extend through the catheter 14 and beyond the distal end of the catheter 14 when the introducer needle 16 is in an insertion position for insertion into vasculature of a patient.

In some embodiments, the catheter system 10 may include a needle hub 18, which may be coupled to the catheter adapter 12 when the introducer needle 16 is in the insertion position. In some embodiments, a proximal end of the introducer needle 16 may be secured within the needle hub 18. In some embodiments, the catheter system 10 may include a needle shield 19. In some embodiments, the catheter system 10 may be integrated or non-integrated. In some embodiments, the catheter system 10 may include the needle shield 19 or any other type of suitable needle safety mechanism.

Referring now to FIG. 2A, in some embodiments, the introducer needle 16 may include a proximal end, a distal tip 20, and a needle lumen 22 extending between the proximal end and the distal tip 20. In some embodiments, the introducer needle 16 may include a wall 24, which may define the needle lumen 22. In some embodiments, the first notch 26 may be formed through the wall 24, and the second notch 28 may be formed through the wall 24. In some embodiments, the second notch 28 may be proximal to the first notch 26. In some embodiments, the wall 24 may include more than two notches.

In some embodiments, the first notch 26 of the introducer needle 16 may be disposed within the catheter 14 when the introducer needle 16 is in the insertion position. In some embodiments, at least a portion of the catheter 14 may be transparent. In some embodiments, presence of the second notch 28 may facilitate pressure-driven blood flow into the catheter 14 for improved flashback and detection of transfixation. In some embodiments, the second notch 28 may improve first needle stick success by improving the quality of flashback.

In further detail, in some embodiments, the catheter system 10 may include a first fluid pathway 30, which may extend from the first notch 26 to the second notch 28 between an outer surface of the introducer needle 16 and an inner surface of a wall 32 forming the catheter 14, and a second fluid pathway 34, which may extend from the first notch 26 to the second notch 28 within the needle lumen 22. In some embodiments, during flashback, blood may flow through the first fluid pathway 30 and/or the second fluid pathway 34. In some embodiments, the first fluid pathway 30 may provide pressure-driven flashback, even after the catheter system 10 is primed. In some embodiments, flashback or proximal blood travel may be faster through the first fluid pathway 30 than the second fluid pathway 34. In some embodiments, flashback through the first fluid pathway 30 may be visible due to the transparency of the catheter 14.

In some embodiments, the second notch 28 may be disposed within the catheter 14 when the introducer needle 16 is in the insertion position. In some embodiments, the second notch 28 may be disposed within the lumen of the catheter adapter (as illustrated, for example, in FIGS. 4A-4B) when the introducer needle 16 is in the insertion position. In some embodiments, a distance between the first notch 26 and the second notch 28 may be greater than a length of the catheter 14, which may facilitate visibility of transfixation.

In some embodiments, the first fluid pathway 30 may have a larger volume than the second fluid pathway 34, which may facilitate faster flashback or proximal blood travel through the first fluid pathway 30 than the second fluid pathway 34. Referring now to FIG. 2B, in some embodiments, a cross-section taken through the catheter system 10 perpendicular to a central axis 40 of the catheter system 10 and between the first notch 26 and the second notch 28 may include a needle lumen area 36 and another area 38 between the outer surface of the introducer needle 16 and the inner surface of the wall 32 of the catheter 14. In some embodiments, the other area 38 may be greater than the needle lumen area 36. In some embodiments, the other area 38 may be greater than the needle lumen area 36 in each cross-section taken through the catheter system 10 perpendicular to the central axis 40 along an entire length between the first notch 26 and the second notch 28.

Figure 2C:
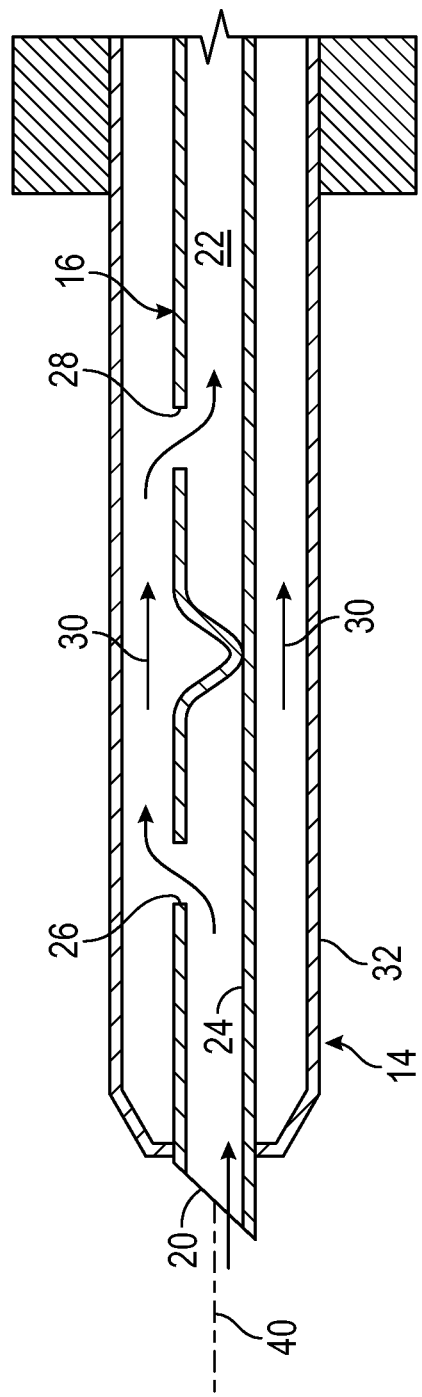
FIG. 2C is a cross-sectional view of the introducer needle of FIG. 2A having an example crimp feature and disposed within the catheter, illustrating the introducer needle in the insertion position, according to some embodiments.

Referring now to FIG. 2C, in some embodiments, a portion of the wall 24 of the introducer needle 16 between the first notch 26 and the second notch 28 may be pinched or crimped such that fluid, such as blood, is prevented from flowing in the needle lumen 22 between the first notch 26 and the second notch 38. In some embodiments, the crimped portion 42 of the wall 24 may facilitate rapid flashback through the first fluid pathway 30.

Figure 2D:
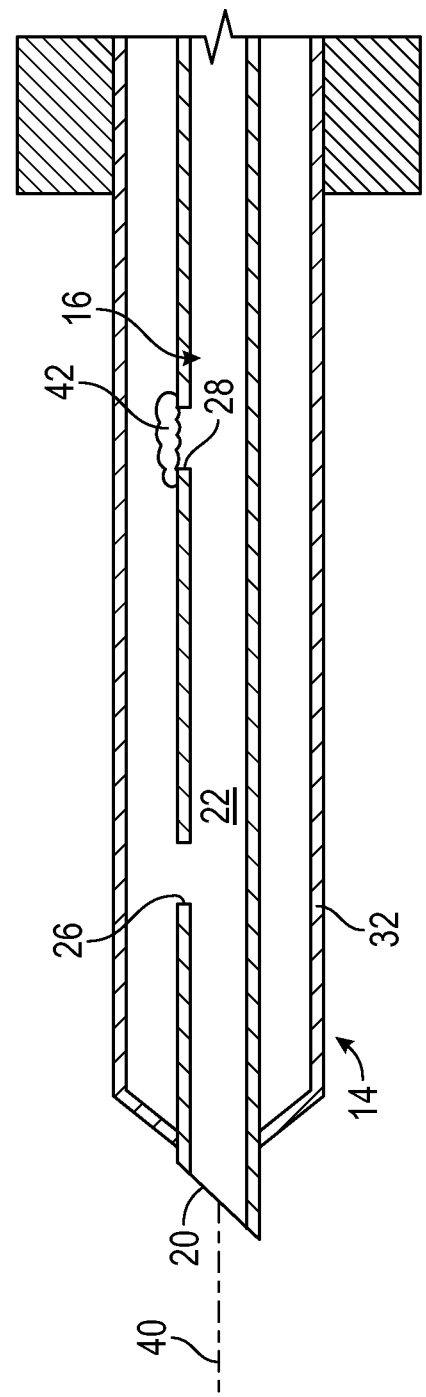
FIG. 2D is a cross-sectional view of the introducer needle of FIG. 2A disposed within the catheter, illustrating the introducer needle in the insertion position and an example plug constructed of a dissolvable material, according to some embodiments.

Referring now to FIG. 2D, in some embodiments, a plug 42, which may be constructed of a dissolvable material, may seal the second notch 28 during priming of the catheter 14. In some embodiments, the plug 42 may be dissolved when the catheter system 10 is introduced into the vasculature of the patient.

Figure 2E:
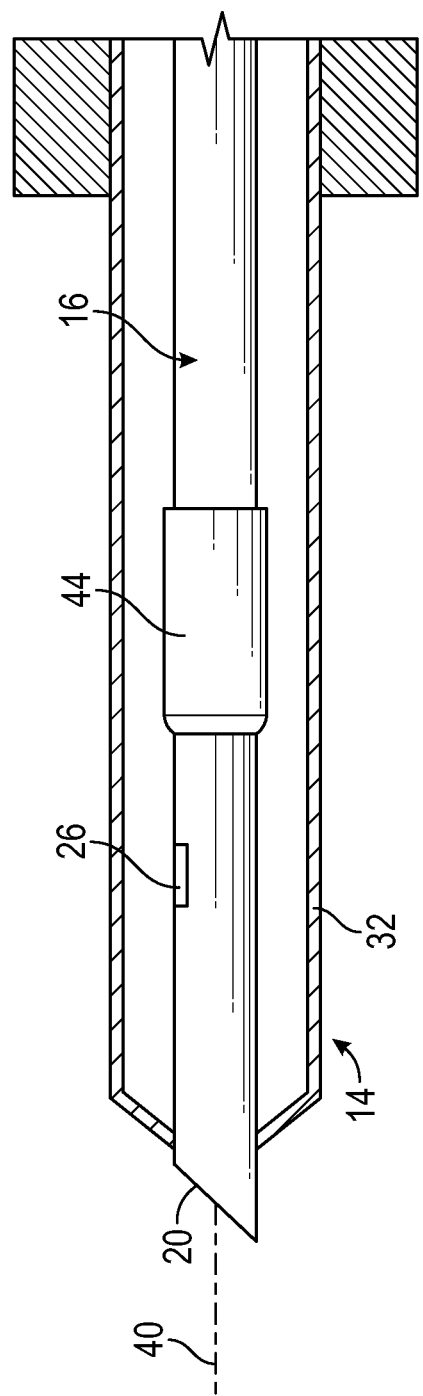
FIG. 2E is a partial cutaway of the introducer needle of FIG. 2A disposed within the catheter, illustrating the introducer needle in the insertion position and a sleeve element constructed of a dissolvable material, according to some embodiments.

Referring now to FIG. 2E, in some embodiments, a sleeve 44, which may be constructed of a dissolvable material, may seal the second notch 28 during priming of the catheter 14. In some embodiments, the sleeve 44 may be dissolved when the catheter system 10 is introduced into the vasculature of the patient.

Referring now to FIGS. 3A-3B, in some embodiments, the catheter system 10 may include a flash chamber 46, which may facilitate flashback. In some embodiments, the flash chamber 46 may be in fluid communication with the needle lumen 22. In some embodiments, the flash chamber 46 may include a gas permeable vent 48. In some embodiments, the flash chamber 46 may be disposed proximal to the proximal end 49 of the introducer needle 16. In some embodiments, the gas permeable vent 48 may provide at least some resistance to air flow. In some embodiments, the flash chamber 46 may be disposed within the needle hub 18, as illustrated, for example, in FIG. 3B. FIGS. 3A-3B illustrate a needle assembly with the needle shield 19 removed, according to some embodiments.

In some embodiments, the catheter 14 may be primed prior to insertion of the catheter 14 and the introducer needle 16 into the vasculature of the patient. In some embodiments, the catheter 14 may be primed when the introducer needle 16 is in the insertion position. In some embodiments, in order to prime the catheter 14, the user may fill the catheter 14 with a priming fluid, such as, for example, saline, to reduce or eliminate any air pockets disposed within the catheter. In some embodiments, the priming fluid may be disposed in a first portion of a needle lumen proximate the first notch 26 and including the distal tip 20 of the introducer needle 16. Additionally, in some embodiments, the priming fluid may be disposed in a second portion of the needle lumen 22 proximate the second notch 28. In some embodiments, when the gas permeable vent 48 provides the resistance, the priming fluid in the first portion may be separated from the priming fluid in the second portion, and air may be disposed between the first portion and the second portion in the needle lumen 22.

In some embodiments, in response to the distal tip 20 of the introducer needle 16 entering the vasculature, blood pressure will drive the flashback into the introducer needle 16. Additionally, in some embodiments, at least some of the flashback may then be driven out of the introducer needle 16 at the first notch 26 and into the catheter 14. Furthermore, in some embodiments, in response to the distal tip 20 of the introducer needle 16 entering the vasculature, the priming fluid outside the introducer needle 16 and within the catheter 14 between the first notch 26 and the second notch 28 may be driven into the introducer needle 16 through the second notch 28 and may eventually reach the flash chamber 46. In some embodiments, in response to the distal tip 20 of the introducer needle 16 entering the vasculature, blood may flow proximally through the introducer needle 16 as well. In some embodiments, the pressure-driven blood flow through the first fluid pathway 30, which may initially be filled with the priming fluid, may be faster than diffusion.

In some embodiments, the flash chamber 46 may include a large, non-restrictive volume, which may facilitate the pressure-driven flow of the priming fluid and/or blood towards or into the flash chamber 46. In some embodiments, a volume of the flash chamber 46 may be large enough to hold the priming fluid disposed outside the introducer needle 16 and within the catheter 14 between the first notch 26 and the second notch 28 and/or the priming fluid that may travel into the flash chamber 46 during priming of the catheter 14. Additionally, in some embodiments, the volume of the flash chamber 46 may be large enough to hold blood when the distal tip 20 of the introducer needle 16 is disposed within the vasculature.

Figure 4A:
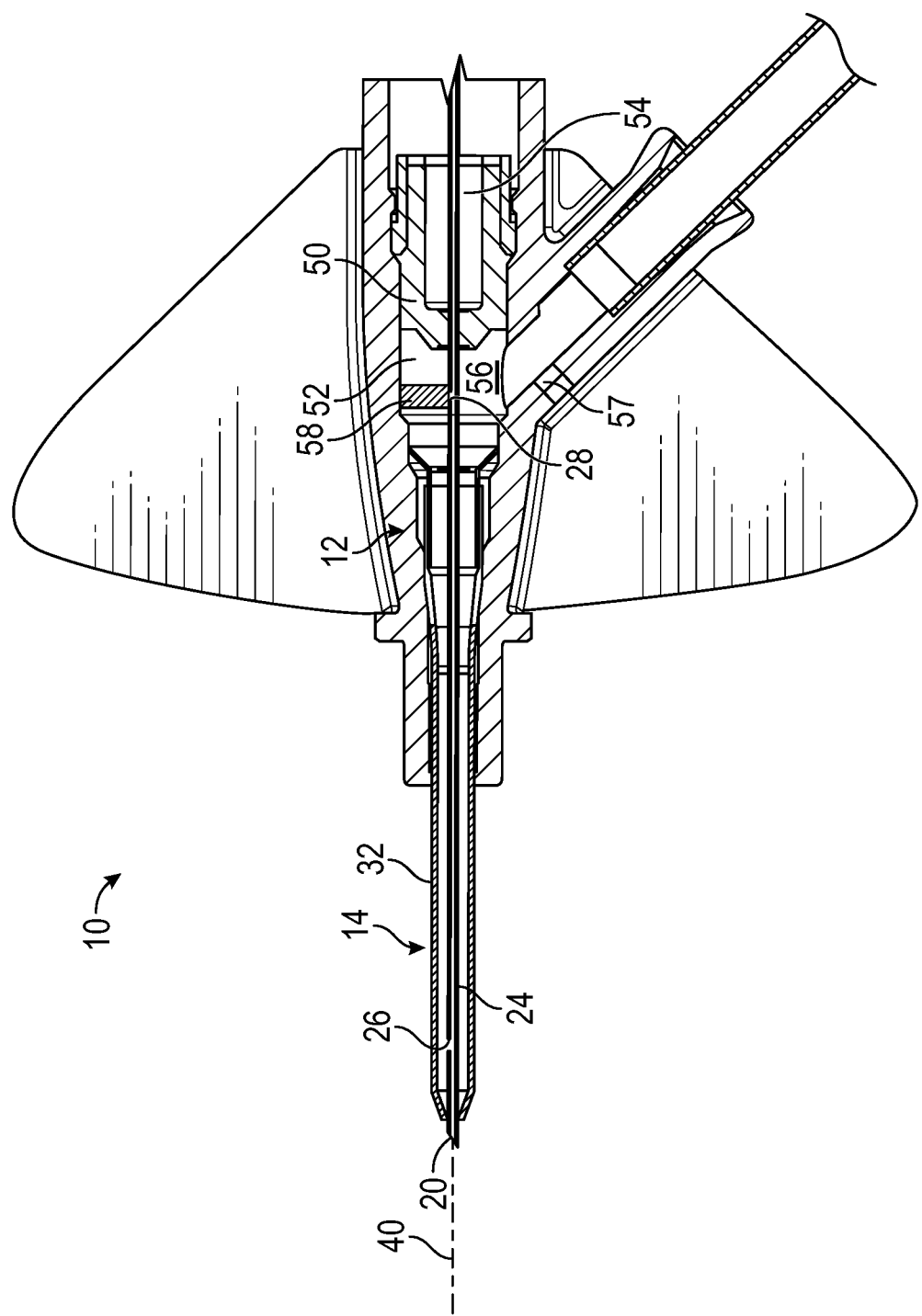
FIG. 4A is a cross-sectional view of the catheter system of FIG. 1A, illustrating the catheter system in the insertion position and an example seal covering an example second notch, according to some embodiments.
Figure 4B:
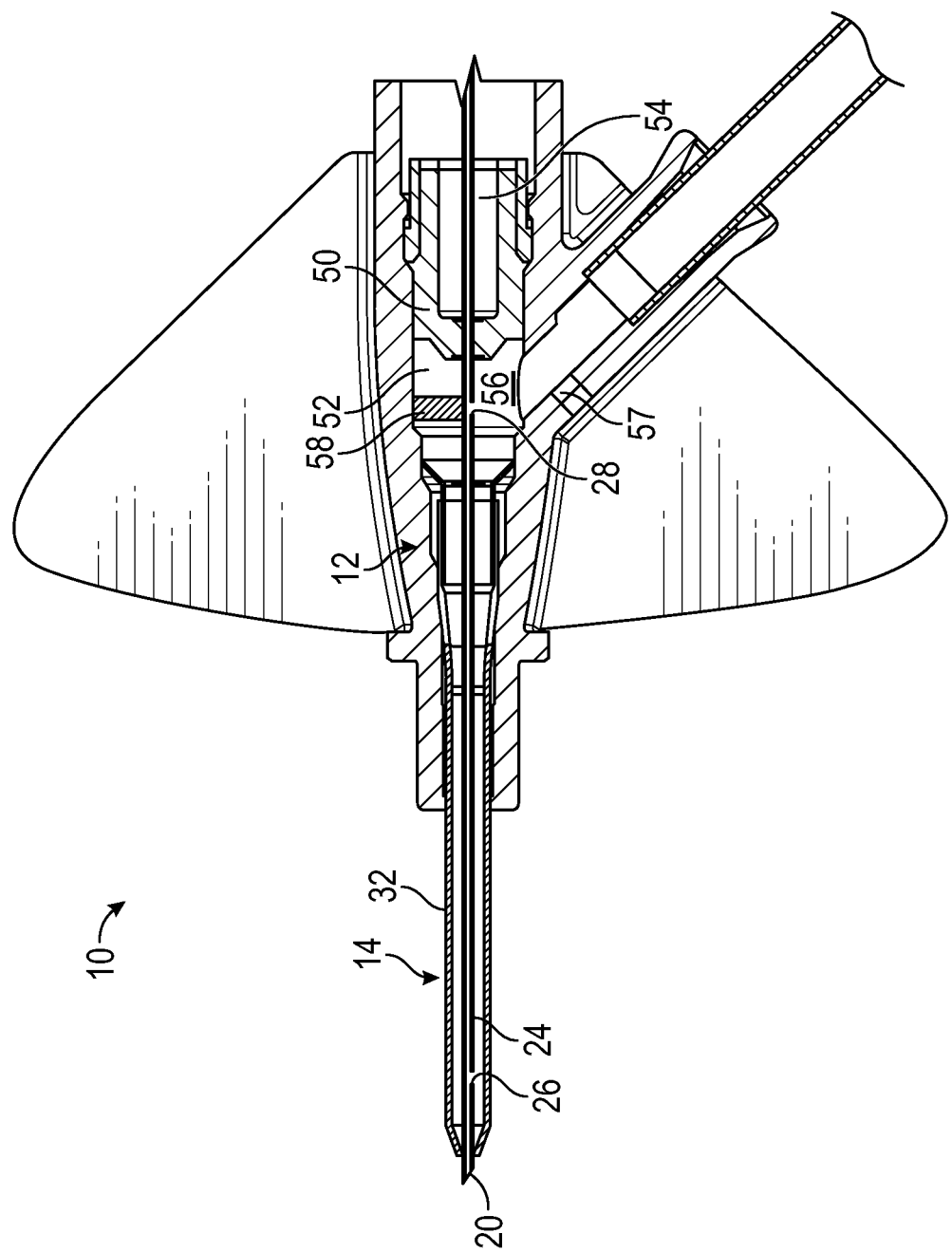
FIG. 4B is a cross-sectional view of the catheter system of FIG. 1A, illustrating the seal removed from the second notch, according to some embodiments.

Referring now to FIGS. 4A-4B, in some embodiments, the catheter system 10 may include a blood control septum 50, which may be disposed within the lumen 52 of the catheter adapter 12. In some embodiments, the septum 50 may divide the lumen 52 of the catheter adapter 12 into a proximal chamber 54 and a distal chamber 56. In some embodiments, the second notch 28 may be disposed distal to the septum 50 when the introducer needle 16 is in the insertion position.

In some embodiments, the catheter adapter 12 may include a gas permeable vent 57, which may be selectively opened and/or closed. In some embodiments, the gas permeable vent 57, which may be disposed through a wall of the catheter adapter 12, may be disposed distal to the septum 50 such that air in the distal chamber 56 may freely flow out of the gas permeable vent 57 when the gas permeable vent 57 is opened. In some embodiments, the gas permeable vent 57 of the catheter adapter 12 may be opened during priming of the catheter 14, which may prevent the priming fluid from being disposed in the first portion of the introducer needle 16 proximate the first notch 26 and/or the second portion 28 of the introducer needle 16 proximate the second notch 28.

In some embodiments, the catheter system 10 may include a seal 58, which may be secured within the lumen 52 of the catheter adapter 12. In these and other embodiments, the portion of the wall of the introducer needle 16 between the first notch 26 and the second notch 28 may be pinched or crimped such that fluid is prevented from flowing in the needle lumen 22 between the first notch 26 and the second notch 28. In some embodiments, the introducer needle 22 may be rotatable from a priming position to the insertion position and/or from the insertion position to the priming position. FIG. 4A illustrates the introducer needle 22 in the insertion position, according to some embodiments, and FIG. 4B illustrates the introducer needle 22 in the priming position, according to some embodiments. In some embodiments, the introducer needle 16 may be disposed in the priming position during priming of the catheter and may be disposed in the insertion position during insertion into the vasculature. In some embodiments, the catheter system 10 may not include the seal 58 and/or the priming and insertions positions may be the same.

In some embodiments, when the introducer needle 16 is in the priming position, the seal 58 may cover or seal the second notch, which may prevent fluid from flowing through the second notch 28. In some embodiments, when the introducer needle 16 is in the insertion position, the seal 58 may not cover or seal the second notch 28 and fluid may flow through the second notch 28. In some embodiments, in response to the second notch 28 being uncovered or unsealed, rapid flashback may occur with blood flowing into the needle lumen 22 via the second notch 28. In some embodiments, the seal 58 may include a septum or flapper.

In some embodiments, the introducer needle 16 may be rotatable between the priming position and the insertion position about the central axis 40 of the catheter system 10, which may extend through the needle lumen 22. In some embodiments, the introducer needle 16 may be rotated by twisting the needle hub 18. In some embodiments, the introducer needle 16 may be rotated in a first direction and/or a second direction opposite the first direction. In some embodiments, the second notch 28 may be aligned with the seal when the introducer needle is in the priming position and the insertion position, as illustrated in FIGS. 4A-4B, for example. In these and other embodiments, the introducer needle 16 may extend a same distance from the distal tip of the catheter 14 when the introducer needle 16 is in the priming position as when the introducer needle 16 is in the insertion position.

The present invention may be embodied in other specific forms without departing from its structures, methods, or other essential characteristics as broadly described herein and claimed hereinafter. The described embodiments and examples are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

All examples and conditional language recited herein are intended for pedagogical objects to aid the reader in understanding the invention and the concepts contributed by the inventor to furthering the art, and are to be construed as being without limitation to such specifically recited examples and conditions. Although implementations of the present inventions have been described in detail, it should be understood that the various changes, substitutions, and alterations could be made hereto without departing from the spirit and scope of the invention.

The invention claimed is:

1. A catheter system, comprising:
    a catheter adapter, comprising a distal end, a proximal end, and a lumen extending therebetween;
    a catheter extending distally from the distal end of the catheter adapter;
    an introducer needle having a wall defining a needle lumen of the introducer needle, a first notch formed through the wall, and a second notch formed through the wall, wherein the second notch is proximal to the first notch and fluid is prevented from flowing between the first notch and the second notch within the needle lumen, wherein the introducer needle extends through the catheter and beyond a distal end of the catheter when the introducer needle is in an insertion position for insertion into a patient; and
    a seal constructed of a dissolvable material configured to dissolve in response to contact with blood, wherein the seal is disposed on top of the second notch to seal the second notch.

2. The catheter system of claim 1, wherein the first notch is disposed within the catheter when the introducer needle is in the insertion position, wherein at least a portion of the catheter is transparent.

3. The catheter system of claim 1, further comprising a flash chamber in fluid communication with the needle lumen, wherein the flash chamber includes a gas permeable vent.

4. The catheter system of claim 1, wherein the catheter adapter further comprises a gas permeable vent, wherein the gas permeable vent is selectively opened and closed.

5. The catheter system of claim 1, further comprising a first fluid pathway, extending from the first notch to the second notch between an outer surface of the introducer needle and an inner surface of a wall of the catheter, and a second fluid pathway, extending from the first notch to the second notch within the needle lumen, wherein flashback is faster through the first fluid pathway than the second fluid pathway.

6. The catheter system of claim 1, wherein a cross-section taken through the catheter system perpendicular to a central axis of the catheter system and between the first notch and the second notch includes a needle lumen area and another area between an outer surface of the introducer needle and an inner surface of a wall of the catheter, wherein the other area is greater than the needle lumen area.

7. The catheter system of claim 1, wherein the second notch is disposed within the catheter when the introducer needle is in the insertion position.

8. The catheter system of claim 1, wherein the fluid is prevented from flowing between the first notch and the second notch within the needle lumen by a crimp or pinch in the introducer needle.

9. The catheter system of claim 1, wherein the first notch does not include a seal.

10. An introducer needle, comprising:
a proximal end, a distal tip, and a needle lumen extending therebetween;
a wall defining the needle lumen;
a first notch formed through the wall;
a second notch formed through the wall, wherein the second notch is proximal to the first notch and fluid is prevented from flowing between the first notch and the second notch within the needle lumen; and
a seal constructed of a dissolvable material configured to dissolve in response to contact with blood, wherein the seal is disposed on top of the second notch to seal the second notch.

11. The introducer needle of claim 10, wherein the fluid is prevented from flowing between the first notch and the second notch within the needle lumen by a crimp or pinch in the introducer needle.

12. A catheter system, comprising:
a catheter adapter, comprising a distal end, a proximal end, and a lumen extending therebetween;
a catheter extending distally from the distal end of the catheter adapter;
a blood control septum disposed within the lumen and dividing the lumen into a proximal chamber and a distal chamber;
an introducer needle having a wall defining a needle lumen of the introducer needle, a first notch formed through the wall, and a second notch formed through the wall, wherein the second notch is proximal to the first notch and fluid is prevented from flowing between the first notch and the second notch within the needle lumen, wherein the introducer needle extends through the catheter and beyond a distal end of the catheter when the introducer needle is in an insertion position for insertion into a patient, wherein the first notch is disposed within the catheter when the introducer needle is in the insertion position, wherein at least a portion of the catheter is transparent, wherein the second notch is disposed distal to the blood control septum when the introducer needle is in the insertion position; and
a seal constructed of a dissolvable material configured to dissolve in response to contact with blood, wherein the seal is disposed on top of the second notch to seal the second notch.

13. The catheter system of claim 12, further comprising a needle hub coupled to the catheter adapter, wherein a proximal end of the introducer needle is secured within the needle hub, wherein the needle hub includes a flash chamber in fluid communication with the needle lumen and proximal to the proximal end of the introducer needle, wherein the flash chamber includes a gas permeable vent.

14. The catheter system of claim 12, wherein the catheter adapter further comprises a gas permeable vent extending through a wall of the catheter adapter distal to the blood control septum, wherein the gas permeable vent is selectively opened and closed.

15. The catheter system of claim 12, wherein the second notch is disposed within the catheter when the introducer needle is in the insertion position.

16. The catheter system of claim 12, wherein the fluid is prevented from flowing between the first notch and the second notch within the needle lumen by a crimp or pinch in the introducer needle.

17. A catheter system, comprising:
a catheter adapter, comprising a distal end, a proximal end, and a lumen extending therebetween;
a catheter extending distally from the distal end of the catheter adapter;
an introducer needle having a wall defining a needle lumen of the introducer needle, a first notch formed through the wall, and a second notch formed through the wall, wherein the second notch is proximal to the first notch, wherein the introducer needle extends through the catheter and beyond a distal end of the catheter when the introducer needle is in an insertion position for insertion into a patient; and
a seal constructed of a dissolvable material configured to dissolve in response to contact with blood, wherein the seal is disposed on top of the second notch to seal the second notch, wherein the first notch does not include a seal.

18. The catheter system of claim 17, wherein the first notch is disposed within the catheter when the introducer needle is in the insertion position, wherein at least a portion of the catheter is transparent.

19. The catheter system of claim 17, further comprising a flash chamber in fluid communication with the needle lumen, wherein the flash chamber includes a gas permeable vent.

20. The catheter system of claim 17, wherein fluid is prevented from flowing between the first notch and the second notch within the needle lumen by a crimp or pinch in the introducer needle.

* * * * *